US00PP17165P2

(12) United States Plant Patent
Tristram

(10) Patent No.: US PP17,165 P2
(45) Date of Patent: Oct. 24, 2006

(54) ***CROCOSMIA* PLANT NAMED 'WALBREYES'**

(50) Latin Name: *Crocosmia×hybrida*
Varietal Denomination: WALBREYES

(76) Inventor: David Tristram, Walberton Nursery, Yapton Lane, Walberton, Arundel (GB), BN18 OAS ( * ) Notice: Subject to any disclaimer, the term of this patent is extended or adjusted under 35 U.S.C. 154(b) by 52 days.

(21) Appl. No.: 11/226,817

(22) Filed: Sep. 13, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new cultivar of *Crocosmia* named 'Walbreyes' that is characterized by an upright clumping habit, short height, and free-flowering sterile yellow/orange flowers with red centers that face reasonably upward. In combination these traits set 'Walbreyes' apart from all other existing varieties of *Crocosmia* known to the inventor.

2 Drawing Sheets

Genus: *Crocosmia.*
Species: ×*hybrida.*
Denomination: Walbreyes.

BACKGROUND OF THE INVENTION

The present invention relates to a new and distinct cultivar of montbretia grown for use as an ornamental herbaceous perennial for the landscape. The new cultivar is known botanically as *Crocosmia* and will hereinafter be referred to as 'Walbreyes'.

'Walbreyes' is an induced hybrid that resulted from a formal long term breeding program that was established by the inventor in Ireland in 1959 and continued to 1972 when the breeding program was moved to England and continued from 1973 to the present time. The objectives of the breeding program were to produce plants that are free-flowering, even when crowded, with reasonably upward facing flowers, good flower size, with a range of flower colors and attractive markings.

The female parent of 'Walbreyes' is an unnamed *Crocosmia* hybrid and the male parent is an unnamed *Crocosmia* hybrid. 'Walbreyes' resulted from a complex series of induced hybridization between the plants *Crocosmia pottsii* (unpatented), *Crocosmia masonorum* (unpatented), *Crocosmia* 'Solfatarre' (unpatented), *Crocosmia* 'His Majesty' (unpatented) and *Crocosmia* 'Emily McKenzie' (unpatented). These induced crosses were conducted by the inventor in a cultivated area of Sussex, England, producing unnamed hybrids that were crossed in further induced hybridization. 'Walbreyes' was selected from the resulting seedlings by the inventor in Sussex in 1998.

'Walbreyes' is a clumping perennial ornamental that is sterile, long blooming, and exhibits yellow/orange flowers with red centres. The closest comparison plant is *Crocosmia* 'Walberton Yellow' (unpatented). The characteristics that distinguish 'Walbreyes' from the comparison plant are plant height and flower color. The distinguishing characteristics of 'Walbreyes', that make it unique from all other *Crocosmia* known to the inventor, are flower color, short height, flower aspect, sterility, and free flowering.

'Walbreyes' was first asexually propagated in 1999 by the inventor in a cultivated area of Sussex, England. The method used for asexual propagation was division. Since that time under careful observation, 'Walbreyes' has remained stable and true to type through successive generations of asexual propagation.

SUMMARY OF THE INVENTION

The following traits have been repeatedly observed and represent the distinguishing characteristics of the new *Crocosmia* variety known as 'Walbreyes'. These traits in combination distinguish 'Walbreyes' from all other existing varieties of *Crocosmia* known to the inventor. 'Walbreyes' has not been tested under all possible conditions and phenotypic differences may be observed with variations in environmental, climatic, and cultural conditions, however, without any variance in genotypes.

1. *Crocosmia* 'Walbreyes' exhibits flowers that face reasonably upward.
2. *Crocosmia* 'Walbreyes' exhibits an upright clumping habit and short height.
3. *Crocosmia* 'Walbreyes' is a perennial ornamental plant for use in containers and the landscape.
4. *Crocosmia* 'Walbreyes' blooms over a long period.
5. *Crocosmia* 'Walbreyes' is sterile.
6. *Crocosmia* 'Walbreyes' is free-flowering.
7. *Crocosmia* 'Walbreyes' exhibits yellow/orange flowers with red centres.
8. *Crocosmia* 'Walbreyes' continues flowering even when crowded.

BRIEF DESCRIPTION OF THE DRAWINGS

The accompanying color drawings illustrate the overall appearance of the new *Crocosmia* variety 'Walbreyes' showing the colors as true as it is reasonably possible to obtain in colored reproductions of this type.

The drawing labeled

Figure 1:
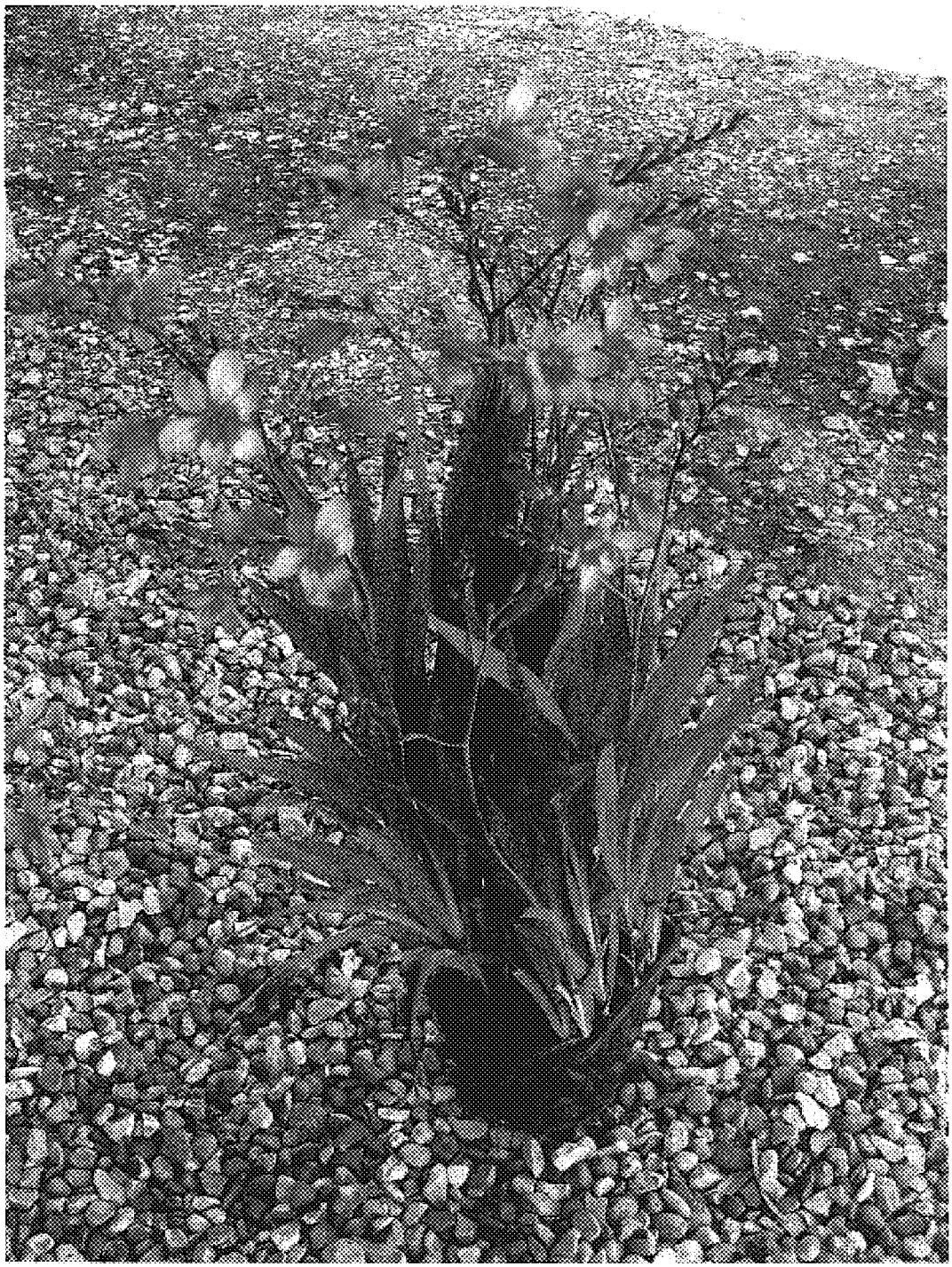
FIG. 1 illustrates the plant from a side perspective.
Figure 2:
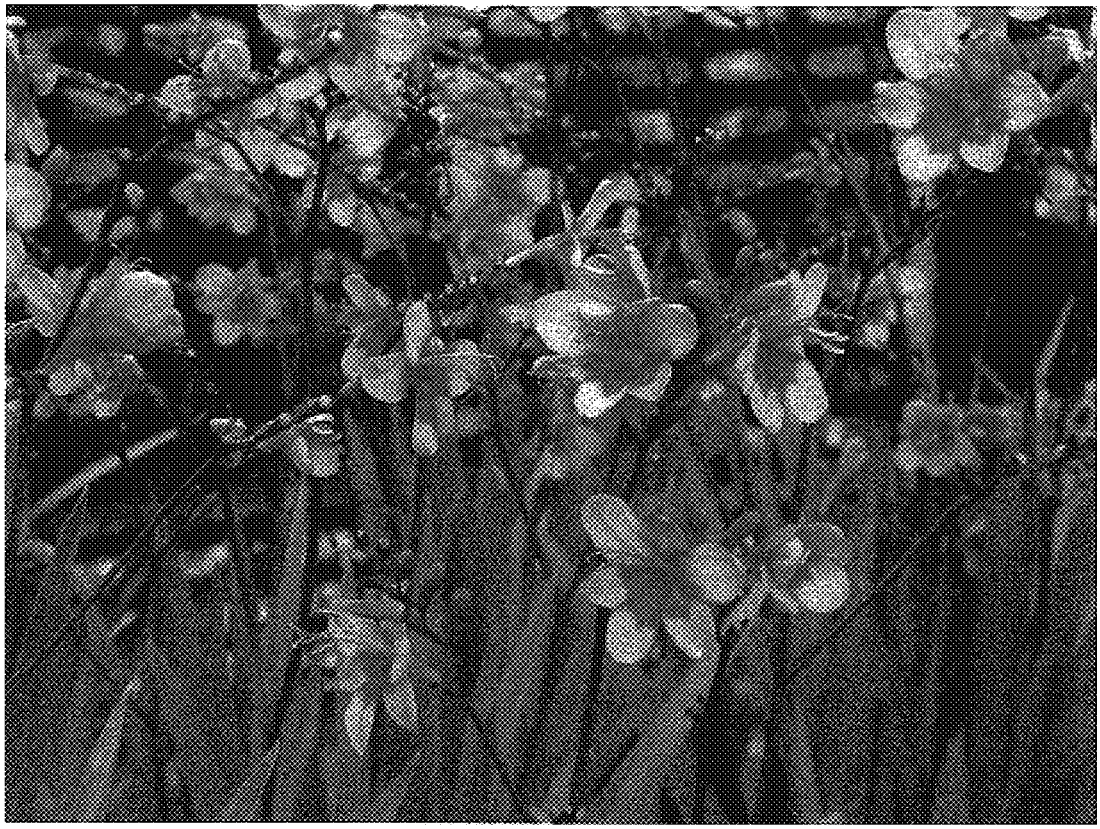

The drawing labeled as FIG. 2 is a close-up view of the flowers.

Colors in the drawings may differ from the color values cited in the detailed botanical description, which more accurately describe the actual colors of the new variety 'Walbreyes'. Drawings were made using conventional techniques and although flower and foliage colors may appear different from actual colors due to light reflectance, they are as accurate as possible by conventional photography.

BOTANICAL DESCRIPTION OF THE PLANT

The following is a detailed description of the new *Crocosmia* cultivar named 'Walbreyes'. Information was compiled in Sussex, UK. Color determinations are in accordance with the 1952 Royal Horticultural Society Colour Chart except where general color terms of ordinary dictionary significance are used. The growing requirements are similar to the species.

Botanical classification: *Crocosmia* 'Walbreyes'.
Species: ×*hybrida*.
Common name: Montbretia.
Use: Ornamental landscape and container plant.
Type: Herbaceous perennial.
Parentage: The hybrid 'Walbreyes' resulted from the induced hybridization between the following parent plants.
- *Female parent plant.*—Unnamed *Crocosmia* hybrid.
- *Male parent plant.*—Unnamed *Crocosmia* hybrid.

Growth rate: Moderately vigorous.
Growth habit: Upright and clumping habit.
Plant height: 50–70 cm. in height at maturity.
Plant width: 30–60 cm. in width at maturity.
Hardiness: USDA Zone 7.
Propagation: Tissue culture and division are used to asexually propagate.
Root system: Thick and fine roots.
Cultural requirements: Plant in full sun or partial sun and ordinary soil, giving water when needed during growth and bloom. Needs some shade in hottest climates.
Pollination requirements: None.
Sexuality: Bisexual.
Diseases or pests: Susceptible to red spider-mite.
Cropping time: Approximately 6 months from division to a one-gallon container.
Seasonal interest: Yellow/orange flowers with red centres.
Blooming season: Summer.
Foliage:
- *Type.*—Deciduous.
- *Leaf shape.*—Linear.
- *Leaf arrangement.*—Alternate.
- *Leaf apex.*—Sharply acute.
- *Leaf attachment.*—Clasping.
- *Leaf division.*—Simple.
- *Leaf margins.*—Entire.
- *Stipules.*—None.
- *Leaf color* (*adaxial surface*).—146A.
- *Leaf color* (*abaxial surface*).—146A
- *Leaf surface* (*adaxial surface*).—Glabrous.
- *Leaf surface* (*abaxial surface*).—Glabrous.
- *Venation pattern.*—Parallel.
- *Color of veins* (*abaxial and adaxial surfaces*).—146A.
- *Leaf length.*—20–40 cm. in length.
- *Leaf width.*—10–35 mm. in width.
- *Leaf fragrance.*—None.

Flower:
- *Flowering months.*—July through September.
- *Inflorescence type.*—Panicle.
- *Number of flowers per peduncle.*—20–60 flowers per peduncle, with 5–20 on each branch.
- *Dimensions of peduncle.*—30–45 cm. in length and 3–5 mm. in width, with branches 10–20 cm long.
- *Peduncle color.*—187A.
- *Peduncle surface.*—Glabrous.
- *Persistent or self-cleaning.*—Self-cleaning.
- *Flower aspect.*—Facing horizontally.
- *Flower shape.*—Tubular.
- *Depth of flower throat.*—15–20 mm. in depth.
- *Diameter across widest part of flower.*—35–50 mm. in diameter across the widest part.
- *Length of flower including calyx, corolla and petals.*—35–45 mm. in length.
- *Flower arrangement.*—Flowers alternate in panicles of 3–15 branches.
- *Number of petals.*—Six in number.
- *Petals fused or unfused.*—Basally fused.
- *Petal shape.*—Oblong.
- *Petal margin.*—Entire.
- *Petal surface.*—Slightly glandular.
- *Petal color* (*fully opened*).—Front: Centre 42A, margin between 23A and 25A on all petals. Reverse: Combination of 28A and 42A.
- *Tube color.*—(Inside) 23B; (outside) 25A.
- *Bud shape.*—Ovate and slightly curved.
- *Bud dimensions.*—4–7 mm. in diameter and 15–22 mm. in length.
- *Color of bud*—A combination of 28A and 42A.
- *Calyx dimensions.*—3–4 mm. in diameter and 3–4 mm. in length.
- *Calyx surface.*—Glandular with microscopic parallel lines present.
- *Calyx color.*—Combination of 187A and 199A.
- *Number of sepals in a calyx.*—Two in number.
- *Shape of sepal.*—Oblong.
- *Sepal apex.*—Acute.
- *Sepal margin.*—Entire.
- *Flower fragrance.*—None.

Reproductive organs:
- *Stamens.*—3 in number.
- *Stamen color.*—Upper part 32A, lower part 21B.
- *Stamen dimensions.*—25–30 mm. in length and 1 mm. in width.
- *Anther color.*—177S.
- *Anther shape.*—Linear.
- *Anther dimensions.*—5 mm in length and 1 to 1.50 mm in width.
- *Pollen color.*—21A.
- *Amount of pollen.*—Moderate amount.
- *Pistils.*—One present.
- *Pistil shape.*—Filament.
- *Pistil dimensions.*—1 mm. in width and 35–45 mm. in length.
- *Color of pistil.*—Upper part is 32A and lower part is 21B.
- *Stigma shape.*—Trifid, with each segment bifid.
- *Stigma dimensions.*—Each segment is 0.5 mm. in width and 3–5 mm. in length.
- *Stigma color.*—32B.
- *Style color.*—32B.
- *Ovary color.*—153B.
- *Ovary shape.*—Oval.

*Ovary dimensions.*—3 mm. in width and 3–4 mm. in height.

*Ovary position.*—Inferior.

Seed: Plant has not been observed to set seed in normal growing conditions and is presumed sterile.

It is claimed:

1. A new and distinct variety of *Crocosmia* plant named 'Walbreyes' as described and illustrated.

* * * * *